United States Patent [19]
Couture

[11] 3,955,405
[45] May 11, 1976

[54] ULTRASONIC NDT SYSTEM WITH FLASHING DISPLAY ALARM

[75] Inventor: John W. Couture, Brookfield Center, Conn.

[73] Assignee: Automation Industries, Inc., Los Angeles, Calif.

[22] Filed: Dec. 7, 1973

[21] Appl. No.: 422,834

[52] U.S. Cl. .............................. 73/67.7; 340/248 F
[51] Int. Cl.² ........................................ G01N 29/04
[58] Field of Search............ 73/67.7, 67.8 R, 67.8 S, 73/67.9, 71.5 US, 67.5 R; 340/248 F, 324 A

[56] References Cited
UNITED STATES PATENTS

| | | | |
|---|---|---|---|
| 3,041,872 | 7/1962 | Brown et al. | 73/67.9 |
| 3,053,080 | 9/1962 | Colten | 73/67.9 |
| 3,226,976 | 1/1966 | Wood et al. | 73/67.9 |
| 3,473,082 | 10/1969 | Kolodnyckij | 340/234 A |
| 3,505,665 | 4/1970 | Lasoff et al. | 340/234 A |
| 3,756,071 | 9/1973 | Dory | 73/67.8 R |

*Primary Examiner*—Richard C. Queisser
*Assistant Examiner*—Stephen A. Kreitman
*Attorney, Agent, or Firm*—William Poms

[57] ABSTRACT

An ultrasonic non-destructive testing system is disclosed wherein electrical signals from a search unit are displayed to visually represent reflections of ultrasonic waves occurring within a work piece or test material. The system includes means for generating an alarm or warning signal informing the operator that an ultrasonic echo has occurred which indicates a possible defect. The alarm causes the display screen to be flashed "on" and "off" at a slow rate in response to a detected ultrasonic echo which exceeds the critical level. The flashing screen signals the operator to make a closer visual inspection of the display, which appears intermittently as the display is flashed on and off.

4 Claims, 5 Drawing Figures

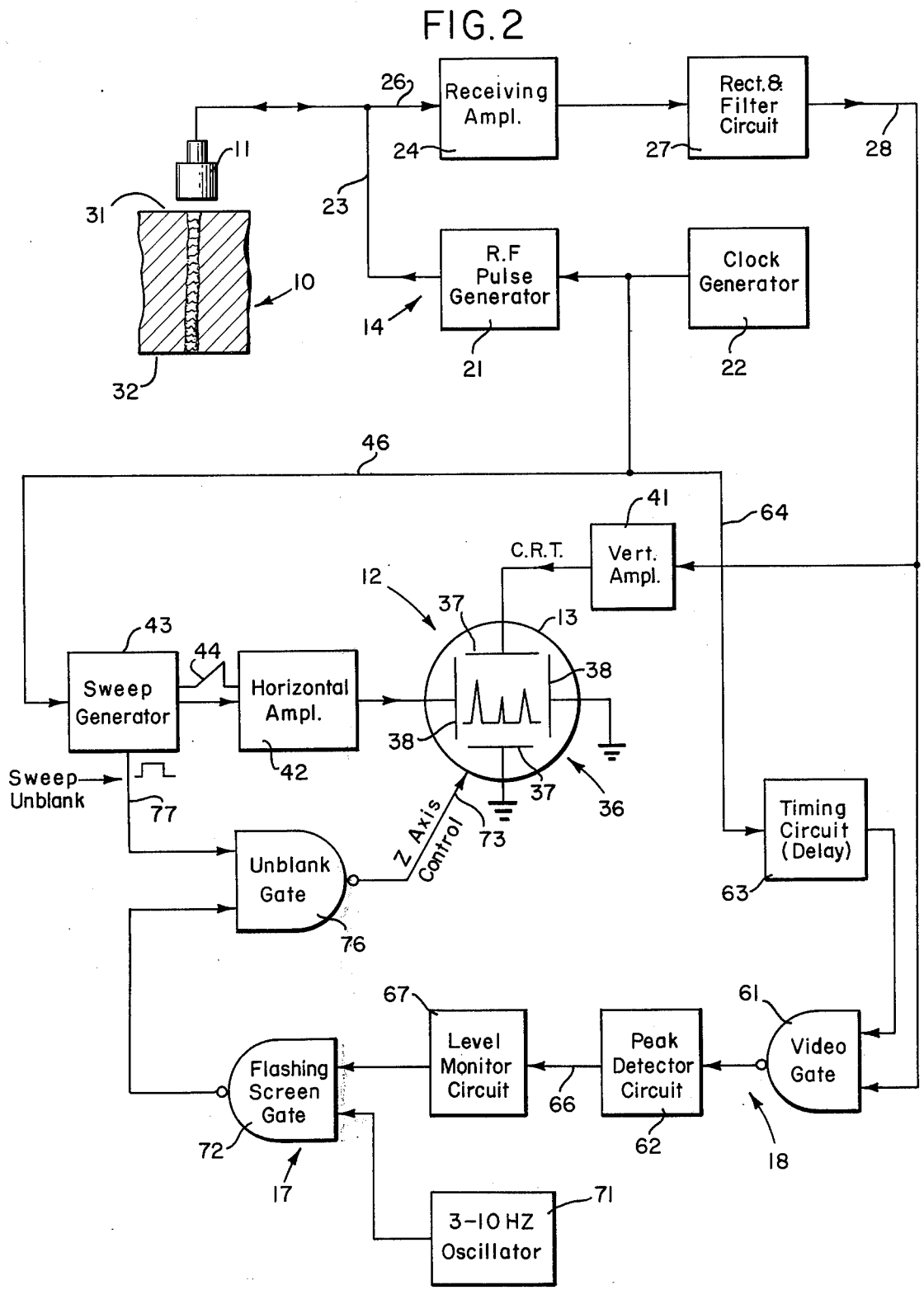

ULTRASONIC NDT SYSTEM WITH FLASHING DISPLAY ALARM

BACKGROUND

One means of inspecting work pieces for internal defects is to utilize an ultrasonic nondestructive testing system. In general these systems employ an electromechanical search unit which transmits ultrasonic energy or waves into the work piece or material under test. If there are internal discontinuities such as flaws or other defects within the material, portions of the ultrasonic energy reflect back to the search unit. The search unit produces an electrical signal representing the magnitude of the reflected ultrasonic energy.

The electrical signals representative of the received ultrasonic energy are typically displayed on a cathode ray tube oscilloscope. These display oscilloscopes are a cathode ray tube adapted specifically for ultrasonic material testing. These devices provide various visual displays representing any abnormalities in the received ultrasonic wave form. For example, in one type of display, a sweep signal synchronized with the pulsing of the transmitting search unit is applied to the horizontal deflection system of the oscilloscope. Electrical signals developed from the receiving search unit are applied to the vertical deflection system. This produces a visual representation of the ultrasonic discontinuities within the work piece. The presence of a defect within the material will appear as a pulse on the oscilloscope screen. The defect's location is indicated by the position of the pulse along the horizontal axis while its magnitude is represented on the vertical scale.

In addition to the cathode ray tube display, it is often desirable to provide a warning or alarm signal in response to detected defects which have magnitudes exceeding a critical level. It is known for example, to provide electrical circuit means for detecting electrical echo signals which exceed a predetermined threshold. The output of such detection circuits may be connected to turn an indicator light on or to sound an alarm.

These indicator or alarm lights are not, however, always seen by the operator who may be concentrating on manipulating the search unit about the surface of the test piece. Additionally, many search units are mounted in automated equipment in which a servo control mechanism moves the search unit along the work piece, freeing the operator to work on other projects. In such cases, the person monitoring the equipment may not see that the indicator light has come on. To provide a higher intensity indicator light is not always practical. Higher intensity warning lights consume a great deal of electrical power, and because the testing equipment is many times portable and battery operated, this of course is an undesirable if not impossible provision.

SUMMARY

The present invention provides means for overcoming the foregoing disadvantages of present signal alarm systems when used with a display oscilloscope. Briefly, the method and apparatus disclosed herein provides a flashing screen generator means for responding to ultrasonic waves exceeding a critical level to cause the display screen of the oscilloscope to rapidly flash on and off. The flashing display screen is readily seen by casual observation of an operator as far as 10 or more feet away from the display device. The flashing warning does not require additional electrical power because the oscilloscope is used for both the display of the received ultrasonic signal and for the visual alarm.

Should the screen begin to flash on and off indicating a possile critical defect, the operator can quickly look at the screen and observe the nature, size and location of the displayed image which appears intermittently.

DRAWINGS

FIG. 2 is a detailed block diagram of the apparatus as shown in FIG. 1 including a flashing screen alarm generator;

Figure 1:
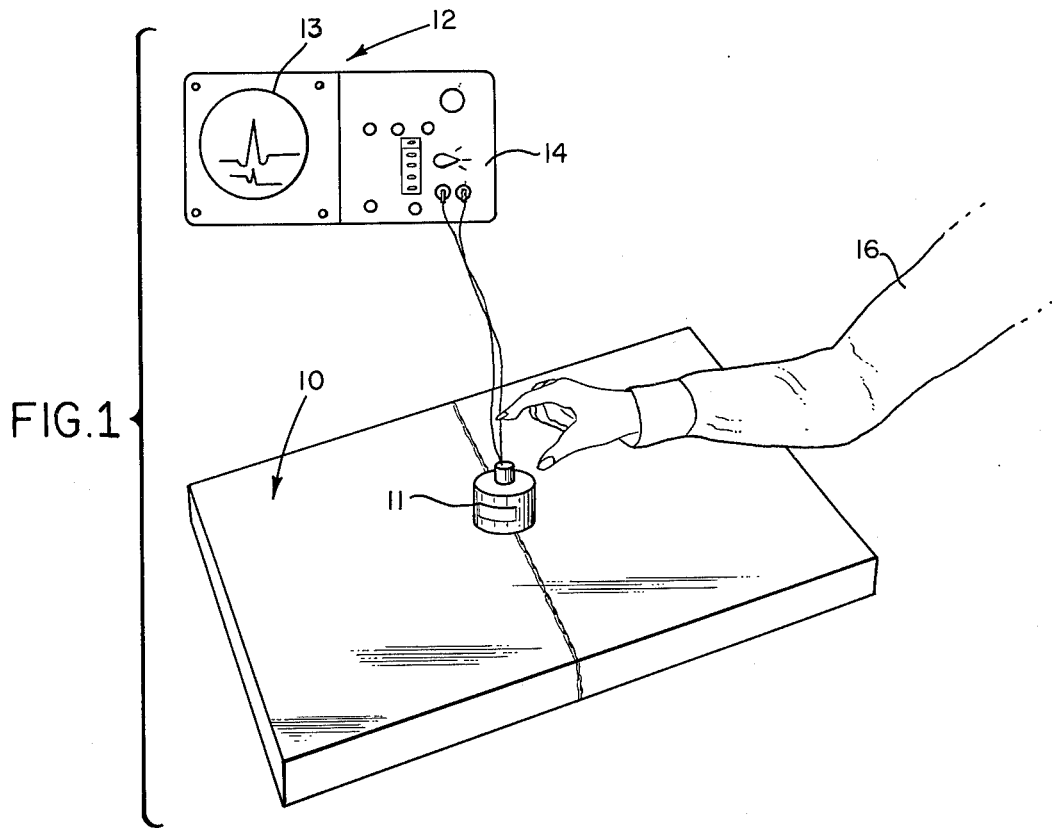
FIG. 1 is a pictorial view of an ultrasonic testing apparatus including a search unit and a cathode ray tube display.
Figures 3A, 3B, 3C:
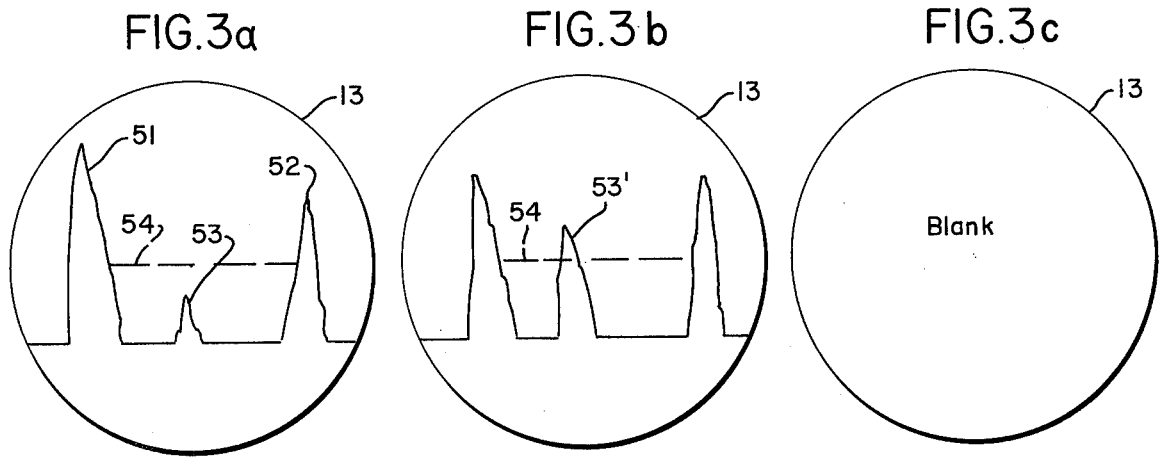

FIG. 3a, 3b 3c are views of the cathode ray tube screen indicating various operating conditions of the apparatus shown in FIGS. 1 and 2.

DESCRIPTION

With reference to the drawings and particularly FIGS. 1 and 2 thereof, an ultrasonic testing apparatus is illustrated for testing a work piece 10. In a pulse-echo operating mode, a search unit 11 including one or more ultrasonic transducers is provided for transmitting short bursts of ultrasonic energy which propagate into work piece 10 as the exterior surfaces thereof are scanned. The transmitted waves of ultrasonic energy are reflected back to search unit 11 by discontinuities associated with the work piece. These discontinuities may represent flaws or defects within the body of the test material.

The reflected ultrasonic signal information may be displayed on any suitable display means such as a cathode ray oscilloscope 12. In this instance, oscilloscope 12 which includes a cathode ray tube screen 13 is combined with various electrical circuits and controls 14 for energizing search unit 12 to transmit the ultrasonic waves and to receive and process the electrical signals representing the ultrasonic echoes. To provide a meaningful display of the ultrasonic echo information, oscilloscope 12 may be synchronized to the electrical pulse circuits which cause search unit 12 to transmit the sound waves. For convenience, it is common to provide oscilloscope 12 together with circuits and controls 14 in a compact portable unit which may be carried out to the field for testing of materials and structures. In such case, the unit may be battery operated.

Although oscilloscope 12 presents an accurate visual representation of the ultrasonic energy relfected from within work piece 10, it is not always practical for the operator 16 to maintain close observation of screen 13 for spotting wave forms indicative of material flaws. For example, the manipulation of search unit 11 over the work piece surface may require the operator to take his eyes off the display screen.

In addition, the oscilloscope 12 may be situated a considerable distance from the work piece 10. As a result it may be very difficult, if not impossible, for the operator to "read" the display on the screen 13. As a consequence, he cannot manipulate the search unit 11 or the work piece 10 and determine from the screen 13 whether a defect is present.

In accordance with the method and apparatus disclosed herein, locating flaws or defects is facilitated by providing a flashing alarm or warning signal on the cathode ray tube screen 13 when an abnormal ultrasonic echo is returned to search unit 11.

This allows operator 16 to concentrate on positioning search unit 11 or to work on other projects if search unit 11 is automated. The flashing screen 13 will instantly alert the operator to a potentially critical defect even though he cannot accurately read the screen from where he is situated. Although the operator may be too far away to read the screen, he can still very easily see the flashing display and then move close to the screen to read it.

With particular reference to FIG. 2, the alarm signal is provided by a flashing screen generator means indicated at 17 for causing the cathode ray oscilloscope display means to flash on and off in response to certain conditions. The conditions which trigger the alarm may be provided by a threshold level signal detection means indicated at 18. This detection means serves to actuate the flashing display warning in response to a detected abnormality in the ultrasonic echo signals returned to search unit 11.

The electrical circuits and controls 14 mounted together with oscilloscope 12 in FIG. 1 may be provided as shown in FIG. 2 by pulse generator means for electrically energizing the transducer means of search unit 11. As above mentioned, search unit 11 responds to such periodic energization or pulsing to transmit the sound waves into the test material. In this instance, the pulse generator means 21 includes an RF pulse generator 21 which is synchronously driven by a clock generator 22. With these components, generator 21 intermittently produces a pulse or burst of radio frequency electrical energy over line 23 which activates the transducer of search unit 11 and causes it to radiate short pulse of ultrasonic energy.

Circuit and control 14 further include receiver means for receiving the electrical signals produced by the transducer of search unit 11 and processing these signals for display on oscilloscope 12. The received electrical signals of course represent the return of echo sound waves reflected by discontinuities associated with work piece 10. In this instance the receiver means includes a receiving amplifier 24 electrically connected to search unit 11 over a line 26. Also the receiver includes a rectification and filtering circuit 27 sometimes referred to as a video detector. Together receiving amplifier 24 and circuit 27 serve to convert the RF signal received over line 26 into a detected or received signal. Sometimes this signal is referred to as a video signal. This video pulse which is available on line 28 is the envelope of the RF signal representing the detected discontinuity in work piece 10.

A number of discontinuities may be associated with the work piece for any given scanning position. Thus the output signal on line 28 may consist of a series of video pulses. For example, in the case of work piece 10 illustrated in FIG. 2, there will be a video pulse representing reflections from both the front surface 31 and rear surface 32 which appear as discontinuities to the ultrasonic energy transmitted from search unit 11. If there is a discontinuity created by a defect within the interior of work piece 10, a video pulse may appear on line 28 sandwiched between the front and rear surface reflections.

Any suitable display means may be provided for displaying the video signal. In the present instance, this includes a cathode ray tube 36 having beam deflection means, here including vertical axis and horizontal axis deflection plates 37 and 38 respectively and vertical and horizontal deflection amplifiers 41 and 42 respectively.

Although several display modes are possible with oscilloscope 12 in this instance the signals representing the ultrasonic echoes are applied to the vertical deflection axis of the cathode ray tube 36 while a sweep signal is applied to the horizontal deflection axis. With reference to FIGS. 3a and 3b, this results in a display on screen 13 of a series of ultrasonic pulses or reflections having a magnitude represented along the vertical axis and a timing represented along the horizontal axis.

To achieve the foregoing operation, the output signal from the receiving amplifier 24 and circuit 27 is connected through the vertical deflection amplifier 41 to deflection plates 37. A sweep generator 43 is connected to apply a sweep signal 44 through horizontal deflection amplifier 42 to plates 38.

To correlate the position of displayed ultrasonic echo signals on the cathode ray tube screen with the physical location of discontinuities represented by such echoes, sweep generator 43 may be synchronized or timed relative to the pulsing of search unit 11.

In the present embodiment sweep generator 43 has a triggering or synchronizing input connected over lines 46 to the output of clock generator 22. This initiates each sweep signal 44 at the same time that RF pulse generator 21 generates a burst of RF energy in response to clock generator 22. Each time an ultrasonic pulse is transmitted into work piece 10, the horizontal sweep of the cathode ray tube traces across screen 13. The rate at which the spot or electron beam travels across the screen depends upon the length of the ultrasonic path to be displayed. Typically the horizontal sweep provided by generator 43 is selected to occupy slightly more time than required for the ultrasonic pulses to propagate to, and be reflected back from, the rear surface 32 of the work piece.

As a result, a typical display of a work piece on screen 13 of the oscilloscope is shown in FIG. 3a. The vertical axis represents the magnitude of the ultrasonic reflection and the horizontal axis represents an increasing time scale and thus the distance of the discontinuity into the work piece. A first echo pulse 51 may represent the discontinuity at the front surface 31 of the work piece. The last echo pulse 52 represents the rear surface reflection. Thus, echo pulse 53 indicates a discontinuity lying somewhere between the front and rear surfaces of the test material, and is perhaps indicative of a defect.

Not all detectable discontinuities or defects within a material are serious. It is many times desirable to search for and locate only flaws having a location and/or magnitude which renders the test object defective. For this purpose the flashing screen generator means 17 and the threshold level detection means 18 are provided. These means serve to produce a warning signal in the event an echo pulse deviates from a predetermined threshold level. For example, in FIGS. 3a and 3b when defect indicating pulse 53 increases to a magnitude of pulse 53' as shown in FIG. 3b and exceeds a threshold level represented by dotted line 54, then the warning system in this embodiment is activated.

The warning system may include an audible alarm such as a buzzer and/or a visual alarm such as a red light. However, in the present instance, it includes means for making all or just a portion of the visual display to flash on and off. This flashing screen forms a various conspicuous display which is readily apparent to the operator.

Threshold level signal detection means 18 may be provided by a test signal gating circuit means connected to receive the output signals from the receiving means and for selectively passing timed portions of such signals to a peak signal detection means. The test signal gating circuit means may be provided by a video gate 61 selectively gating the output of circuit 27 to peak detector circuit 62 in response to a timing signal from timing circuit 63.

Timing circuit 63 is connected back to clock generator 22 over a line 64 and serves to provide an enable signal to gate 61. The leading and trailing edge of this enable signal may be adjustable relative to the clock time determined by generator 22. Such adjustability serves to enable gate 61 for a selected time interval which may be for example placed between the echoes from the front and rear surfaces of the test piece.

With reference to FIGS. 3a and 3b, the echo pulses 51 and 52 from the front rear surface discontinuities of work piece 10 are likely to exceed a threshold level of seriousness for echoes occurring within the body of the test specimen. Thus it is necessary to eliminate or block these front and rear surface reflections from the threshold level detection means. The timing circuit 63 of the gating circuit means may be set to achieve this objective.

In response to those echo pulses which do pass through gate 61, peak detection circuit 62 assumes a level at output 66 representing the peak magnitude of the pulse. Circuits capable of assuming a substantially steady state output representing the peak of intermittently occurring pulses are well known in the art and a detailed description of this circuit is unnecessary here.

The threshold level detection means further includes a level monitor circuit means, here provided by circuit 67. This level monitor circuit means may for example be provided by a Schmitt trigger circuit. Such a circuit is responsive to the output level on line 66 from peak detection circuit 62 to assume one or the other of two stable states. Circuit 67 is normally in its first stable state and only assumes its second stable state when the signal level on line 66 exceeds a predetermined threshold value. Furthermore, circuit 67 remains in the second stable state only so long as the signal on line 66 remains above this threshold magnitude. Typically the threshold level of circuit 67 may be adjusted to suit the application.

The output of level monitor circuit 67 serves to enable the flashing screen generator means and cause it to couple a warning flashing signal to the oscilloscope screen.

Although the threshold level signal detection means described here is primarily adapted to detect flaws within the material which exceed a predetermined magnitude, in general any circuit means which is capable of detecting an abnormality in the reflected ultrasonic energy wave forms may be used. For example, the return of large magnitude reflections from a particular work piece may indicate the nominal or expected work piece condition. If the magnitude of such an echo, however, decreases below the expected level, this may represent the presence of a flaw. In such case, it is desirable for the threshold level signal detection means to sense an abnormally low level signal before the flashing screen alarm is triggered.

Flashing screen generator means 17 is in this instance provided by an oscillator means capable of producing a relatively low frequency intermittent or alternating signal. In this instance, an oscillator 71 is provided. The output frequency range of the oscillator is not critical; however, for example, in this instance an output frequency of approximately 3 to 10 cycles is employed. The output of oscillator 71 is selectively connected to an electron beam intensity control means of oscilloscope 12 to cause a fluctuation of the intensity of the electron beam or an intermittent blanking thereof on screen 13. This results in a conspicuous, brightly flashing display to alert the operator to the presence of a possible defect. It has been found that such a flashing alarm can be easily seen from far in excess of 10–15 feet or more from the oscilloscope, and more when the operator approaches closer to the display, he can still read it easily while it is flashing.

More particularly, and in this instance, the output of oscillator 71 is selectively connected by a flashing screen gating circuit means, here in the form of gate 72, to the beam intensity control means. Here the beam intensity control means is provided by the Z axis control 73 of oscilloscope 12. The Z axis control 73 may merely be provided by the grid control of the electron gun incorporated in cathode ray tube 36.

In this instance, the gated oscillator output passed through gate 72 in response to level monitor circuit 67 and is fed to an unblanking gate 76. Gate 76 provides for overriding the normal unblanking signal associated with the horizontal sweep circuitry. According to this operation, the electron beam of cathode ray tube 36 is normally blanked off. The display is provided by applying a sweep unblanking signal to the axis control 73 from an output line 77 from sweep generator 43. This is a synchronous signal which serves to "unblank" or enable the electron beam to be presented on the screen of the oscilloscope during the horizontal trace interval.

Under normal display conditions, the unblanking signal from output line 77 is passed by gate 76 to and for proper unblanking or the Z axis control 73. However, when gate 72 is enabled by the output of circuit 67, the oscillating or alternating signal output from oscillator 71 intermittently disables gate 76. Thus, the gate intermittently blocks the unblanking signal from reaching the beam intensity control of the cathode ray tube.

The interruption of the unblanking signal occurs at a frequency corresponding to that of oscillator 71 which is substantially lower than the typical horizontal scanning frequency. Accordingly, the full display of the echo pulses appears intermittently on the oscilloscope screen. This creates not only the flashing alarm or warning signal, but also enables the operator to see the intermittently appearing display and immediately determine the nature of the abnormal ultrasonic reflection.

This operation is illustrated by FIGS. 3b and 3c. The display on screen 13 alternates between the full displayed presentation shown in FIG. 3b and the blank screen of FIG. 3c.

While only one particular embodiment of the present invention has been disclosed herein, it will be readily apparent to persons skilled in the art that numerous changes and modifications may be made thereto without departing from the spirit of the invention.

For example, any type of visual display device may be used. It is not essential to use a cathode ray tube. In addition, although the present embodiment discloses and makes reference to the entire display flashing on and off, it should be readily apparent that just preselected portions of the display may be made to flash on and off.

Accordingly, the foregoing disclosure and description thereof are for illustrative purposes only and do not in any way limit the invention which is defined only by the following claims.

I claim:

1. An electronic testing apparatus of the type including a search unit which responds to ultrasonic test waves in a test material to produce electrical test signals, comprising:

cathode ray oscilloscope display means having beam deflection means and beam intensity control means, said deflection means being connected to receive said electrical test signals from said search unit for displaying such signals on a screen of said cathode ray tube;

threshold level signal detection means connected to receive said electrical signals from said search unit to detect the presence of electrical signals exceeding a predetermined level; and flashing screen generator means connected between said detection means and said beam intensity control means of said display means to cause said beam to fluctuate in intensity in response to the occurrence of an electrical test signal exceeding said threshold level, whereby a flashing display is produced on said display means as an alarm or warning signal, said threshold level detection means includes, test signal gating circuit means connected to receive said electrical test signals from said search unit and to pass selectively timed portions thereof, peak signal detector means connected to said test signal gating circuit means for assuming a signal level corresponding to the peak values of those portions of test signals passed by said gating circuit means, and level monitor circuit means connected to said peak signal detector means and having first and second states, said monitor means normally being in its first state and assuming said second state only in response to the signal level of said peak signal detector means assuming a predetermined threshold magnitude, and said flashing screen generator means including, oscillator means, flashing screen gating circuit means having inputs connected to said level monitor means and said oscillator means and having an output connected to said beam intensity control means for causing said beam to vary in intensity in response to said oscillator means, only during the second state of said level monitor means said cathode ray tube display means further includes a sweep generator means connected to said deflection means together with said signal from said search unit for causing the electron beam to sweep across the screen of said display means simultaneously with a change in beam position caused by the test signal, said sweep generator means having blanking signal means for connection to said beam intensity control means, and said flashing screen generator means further comprising a blanking override gating means connecting said blanking signal means from said sweep generator and the output of said flashing screen gating means to said beam intensity control means, whereby the alternating signal output from said flashing screen gating means during the second state of said level monitor means overrides the normal blanking operation of said cathode ray tube display means and causes the display on said screen to flash on and off as said alarm or warning signal.

2. The apparatus of claim 1 wherein said display means being further defined by said deflection means having first axis deflectors and second axis deflectors, said first axis deflectors being connected to receive the test signal from said search unit and said second axis deflectors being connected to said sweep generator means such that said first and second axis deflectors simultaneously deflect the electron beam to display the test signal over a time base.

3. The apparatus of claim 1 said sweep generator means having an operating frequency which substantially exceeds the frequency of said oscillator means.

4. The apparatus of claim 3 said frequency of said oscillator means being in the range of 3–10 hertz.

* * * * *